United States Patent [19]

Macecek et al.

[11] Patent Number: 5,481,916
[45] Date of Patent: Jan. 9, 1996

[54] COMBINED ULTRASONIC AND ROTATING EDDY CURRENT PROBE AND METHOD OF NON-DESTRUCTIVE TESTING OF MATERIALS

[75] Inventors: Mirek Macecek, Toronto; Alec Florei, Brampton; William R. Sturrock, Victoria, all of Canada

[73] Assignee: TSI Sensor Incorporated, Sydney, Canada

[21] Appl. No.: 279,116

[22] Filed: Jul. 22, 1994

[51] Int. Cl.⁶ .................................................. G01N 29/10
[52] U.S. Cl. ............................................ 73/601; 324/226
[58] Field of Search ............................ 73/601, 622, 627, 73/629, 643, 618, 620, DIG. 1, DIG. 3; 324/226, 227, 262

[56] References Cited

U.S. PATENT DOCUMENTS

| | | | |
|---|---|---|---|
| 3,453,872 | 7/1969 | Botsco | 73/69 |
| 3,600,934 | 8/1971 | Hendrix | 73/67.2 |
| 3,886,793 | 6/1975 | Cramer et al. | 73/601 |
| 4,055,989 | 11/1977 | Henry, Jr. et al. | 73/588 |
| 4,208,917 | 6/1980 | Aoyama et al. | 73/644 |
| 4,307,615 | 12/1981 | Robinson | 73/643 |
| 4,495,587 | 1/1985 | Plante et al. | 324/226 |
| 4,578,999 | 4/1986 | Abend et al. | 73/643 |
| 4,710,710 | 12/1987 | Flora et al. | 324/220 |
| 4,772,849 | 9/1988 | Tedder | 324/220 |
| 4,856,337 | 8/1989 | Metala et al. | 73/601 |
| 4,955,235 | 9/1990 | Metala et al. | 73/601 |
| 5,025,215 | 6/1991 | Pirl | 324/220 |
| 5,059,904 | 10/1991 | Mazzone et al. | 324/226 |
| 5,062,298 | 11/1991 | Falcoff et al. | 73/597 |
| 5,161,413 | 11/1992 | Junker et al. | 73/634 |
| 5,225,148 | 7/1993 | Desruelles | 376/245 |
| 5,237,874 | 8/1993 | Latimer et al. | 73/621 |
| 5,285,689 | 2/1994 | Hapstack et al. | 73/623 |
| 5,333,502 | 8/1994 | Clark, Jr. et al. | 73/601 |

*Primary Examiner*—Hezron E. Williams
*Assistant Examiner*—Richard A. Moller
*Attorney, Agent, or Firm*—Kvas Miller Everitt

[57] ABSTRACT

An apparatus, for non-destructively testing for flaws in materials, having a housing assembly with a rotor and a stator for passing over the testing material, an ultrasonic probe fixed to the stator, and an eddy current probe mounted on the rotor. In operation the rotor rotates the eddy current probe about the ultrasonic probe and an indexing coil on the ultrasonic probe monitors the relative position of the eddy current probe. The rotating eddy current probe generates eddy currents in the testing material such that internal flaws effect the normal feed back to the probe. Changes in this feed back are monitored to determine, in conjunction with the indexing coil, the existence and location of flaws in the testing material. In the preferred embodiment a rotary transformer electromagnetically bonds the rotating eddy current probe to the housing stator. Reflected signals received back by the ultrasonic probe are also monitored to determine the existence of flaws, more readily detected by ultrasonic testing, below the probe.

22 Claims, 2 Drawing Sheets

COMBINED ULTRASONIC AND ROTATING EDDY CURRENT PROBE AND METHOD OF NON-DESTRUCTIVE TESTING OF MATERIALS

FIELD OF THE INVENTION

This invention relates to devices of the type used for the non-destructive testing of materials and in particular to such devices which utilize an ultrasonic probe with a revolving eddy current probe. The invention also relates to a method of testing for flaws in materials utilizing such a device.

BACKGROUND OF THE INVENTION

It has long been recognized that the early detection of flaws, both superficial and internal, in metals and similar materials is critical to the prevention of catastrophic failures and the consequences of such failures. For example, the integrity of welds, joints and load bearing structures can be severely compromised through the existence of flaws in their composite materials. Obviously the detection of flaws in such circumstances is of considerable concern from an economic, performance and safety standpoint. Flaws in materials utilized in the nuclear, avionics, and civil engineering construction industries can carry an even greater significance due to the relative impact that a material failure can have in these industries.

In an attempt to reduce the incidence of failures, materials scientists have developed a number of different methods to test for flaws. Flaws may consist of internal abnormalities in metals or materials, superficial irregularities including pitting and corrosion degradation, internal or external stress fractures, flaws from annealing or other heating and cooling processes, or a variety of other imperfections that may exist internally or superficially in a material. In some cases the existence of flaws is readily apparent from a visual inspection, however, in many instances a mere visual inspection is insufficient. This is particularly the cases where a flaw is completely internal and not detectable through conventional methods. These so called invisible flaws often tend to be the cause of the most damaging failures since failure occurs unexpectedly.

Devices such as high powered microscopes and X-ray machines have been developed to assist in the early detection of flaws of this nature. While each of these methods proved to be useful they also suffered from somewhat obvious limitations and inherent problems. Microscopes were useful to detect surface flaws but provide no assistance in locating internal abnormalities. X-ray machines proved to be difficult to operate, expensive and suffered from the limitations and concerns of devices operating with the use of a source of radiation.

To overcome the limitation of these methods of testing, a technique using eddy current excitation was developed. In this technique an eddy current probe coil is subjected to alternating current to create a time varying magnetic field. When the magnetic field is directed onto a metallic surface, eddy current are induced within the metal. These eddy currents then produce their own magnetic fields which have the effect of impeding the time varying magnetic field generated by the probe coil. Abnormalities or flaws in the metal tend to prevent the creation of eddy currents, hence having an effect on the impedance of the time varying magnetic field of the probe. Accordingly, through monitoring the impedance variation in the coil of the eddy current probe it is possible to detect the incidence of internal flaws within the metal.

Although eddy current probes were found to be a significant improvement in non-destructive testing over prior methods they suffered from their own inherent problems. Eddy current testing proved to be useful to detect cracks or flaws oriented generally perpendicular to the probe but did not reliably detect some forms of degradation and could not discriminate between combinations of different types of flaws that were found in the same position. As a result, the use of ultrasonic testing was introduced. In ultrasonic testing, an ultrasonic probe is positioned next to the testing material and the material is subjected to an ultrasonic beam which is reflected by flaws and analyzed. Such ultrasonic probes have been found to be particularly useful to detect flaws arranged horizontally relative to the beam and also are especially effective in detecting flaws where eddy currents are least effective. Unfortunately ultrasonic probes are also not without their limitations; most notably the relatively slow speed at which they must be moved along the testing material, and the need for direct contact, to maintain local sensitivity (when compared to eddy current probes) and their relative inability to detect flaws arranged generally parallel to the ultrasonic beam.

To combine the advantages of each of the eddy current and ultrasonic testing procedures, others have combined both an eddy current probe and an ultrasonic probe into a single device. Such devices have generally been restricted to very specific and limited uses, and particularly for testing the integrity of the walls of heat exchanger tubes in thermal generators in the electrical generation industry. Typically a carrier having both an eddy current and an ultrasonic probe fixed thereon would be inserted into a tube to inspect the tube's walls. The difficulty that is encountered in this application is that to examine the entire surface of the tube a number of eddy current and ultrasonic probes, each directed radially outward, have to utilized. In the alternative, a means of rotating the carrier has to be employed so that coverage of the entire surface is achieved. The use of a rotating carrier has the unfortunate disadvantage of either sacrificing local sensitivity of the ultrasonic testing or sacrificing the coverage available to the eddy current testing due to the variation in the effective rates at which each type of probe operates. Since the consequences of failing to detect a flaw are significant, it is usually opted to reduce coverage and maintain local sensitivity. The result of this is that the overall cost and time expended on testing increases significantly. Furthermore, the configuration of known and existing devices utilizing both eddy current and ultrasonic probes is limited to the testing of the walls of small tubes such as those in steam generators. Such devices do not lead themselves to applications beyond these types of limited uses.

SUMMARY OF THE INVENTION

The invention therefore provides an apparatus for the non-destructive testing of materials which overcomes these limitations by allowing for increased coverage without sacrificing local sensitivity and also allowing for use in applications other than the testing of tubes or pipes.

Accordingly, in one of its aspects the invention therefore provides an apparatus for non-destructively testing for flaws in materials, the apparatus comprising: a housing assembly for passage over the surface of said material to be tested, said housing assembly including a rotor and a stator; an ultrasonic probe, fixedly mounted on said stator of said housing assembly, for transmitting ultrasonic energy to said material to be tested and for receiving ultrasonic energy reflected back toward said ultrasonic probe; an eddy current probe, mounted on said rotor of said housing assembly, for the generation of eddy currents in said material to be tested; and, rotating means for rotationally moving said eddy current probe about said ultrasonic probe.

In another aspect the invention provides an apparatus for non-destructively testing for flaws in materials, the apparatus comprising: a housing assembly for passage over the surface of said material to be tested, said housing assembly including a rotor and a stator; an ultrasonic probe, fixedly mounted on said stator of said housing assembly, for transmitting ultrasonic energy to said material to be tested and for receiving ultrasonic energy reflected back toward said ultrasonic probe; an eddy Current probe, mounted on said rotor of said housing assembly, for the generation of eddy currents in said material to be tested; and, rotating means for rotationally moving said eddy current probe about said ultrasonic probe; the apparatus further including indexing means to monitor the rotational position of the eddy current probe relative to the ultrasonic probe and a rotary transformer electromagnetically bonding the eddy current probe on the housing rotor to the housing stator.

In yet a further aspect the invention provides a method for non-destructively testing for flaws in materials, the method comprising the steps of: passing a housing assembly containing an ultrasonic probe over the surface of said material to be tested; simultaneously rotating an eddy current probe, directed to the surface of the material to be tested, about said ultrasonic probe at a fixed and known rate of revolution; monitoring the position of said rotating eddy current probe relative to said ultrasonic probe through the use of an indexing means operating between said ultrasonic and said eddy current probes; and, monitoring the output signals from said ultrasonic and said eddy current probes.

Further aspects and advantages of the invention will become apparent from the following description taken together with the accompanying drawings.

BRIEF DESCRIPTION OF THE DRAWINGS

For a better understanding of the present invention, and to show more clearly how it may be carried into effect, reference will now be made, by way of example, to the accompanying drawings, which show the preferred embodiment of the present invention in which.

DESCRIPTION OF THE PREFERRED EMBODIMENT

Figure 1:
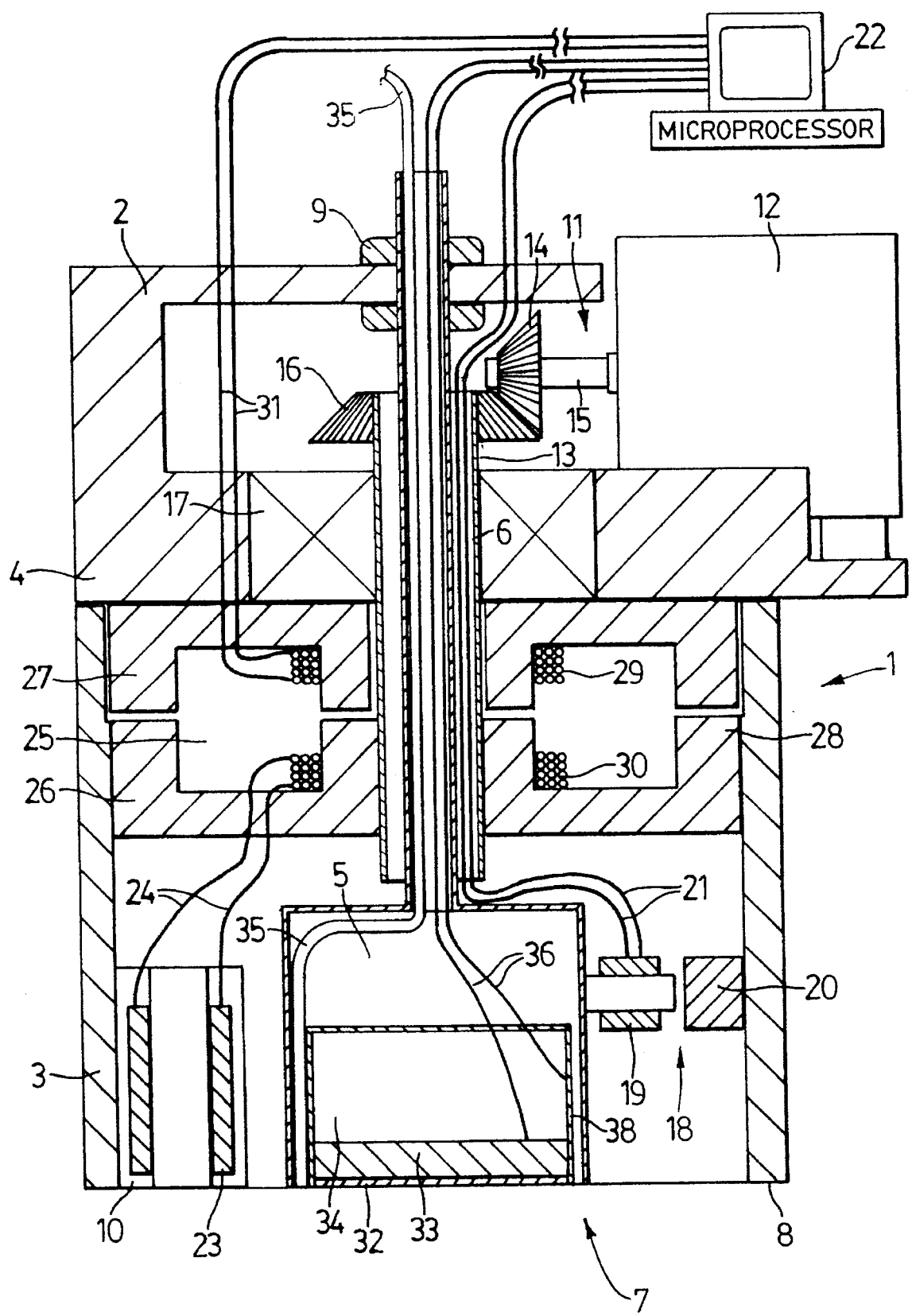
FIG. 1 is a cross-sectional view of the apparatus of the present invention.

FIG. 1 shows, in sectional view, a testing device or apparatus, according to the present invention, generally noted as 1. The testing device 1 is comprised of a housing 2 having a rotor 3 and a stator 4. As can be seen from FIG. 1, housing rotor 3 is generally hollow and cylindrical in shape and situated immediately below the stator 4. A cylindrical central bore 6, passing through the stator, accommodates an ultrasonic probe 5 that extends through the stator 4 and into the hollow rotor 3 with the lower end 7 of the ultrasonic probe 5 approximately flush with the outer end 8 of the housing rotor 3. A bushing 9 secures and fixes the ultrasonic probe 5 in stator 4. An eddy current probe, generally noted at 10, is mounted on the interior surface of the rotor 3. In the preferred embodiment the housing 2 would be constructed from plastic for corrosion resistance and to minimize cost and weight, however, it will be appreciated that a wide variety of other construction materials could equally be employed.

Rotation of the housing rotor 3, and hence the eddy current probe 10 mounted on the rotor 3, is accomplished by rotating means 11. In the preferred embodiment, rotating means 11 comprises a motor 12 that drives a hollow shaft 13 connected to rotor 3. Typically motor 12 will be electrically operated, however, it will be appreciated that it could equally be pneumatic or hydraulic. Referring to FIG. 1, motor 12 is mounted on housing stator 4 with a drive gear 14 situated on its shaft 15. Drive gear 15 meshes with a corresponding gear 16 on hollow shaft 13 such that activation of motor 12 causes gears 14 and 15 to rotate rotor 3. To facilitate with the rotation of rotor 3 a bearing 17 is mounted about the central bore 6 in stator 4. Bearing 17 also serves as a means hold rotor 3 next to stator 4 such that both primary pieces of housing 2 remain intact.

Also mounted on the inner surface of rotor 3 is an indexing means 18 to monitor the rotational position of the eddy current probe 10. Indexing means 18 is comprised of an indexing coil 19, shown in FIG. 1 as positioned on the outer surface of the lower portion of ultrasonic probe 5, and an indexing magnet 20 positioned radially opposite to indexing coil 19 on the inner surface of rotor 3. A pair of electrical wires 21 are connected to indexing coil 19.

In operation, as motor 12 drives gears 14 and 16 causing rotor 3 to rotate about ultrasonic probe 5 mounted on stator 4, indexing magnet 20 also rotates about ultrasonic probe 5 and indexing coil 19. With every revolution of rotor 3, indexing magnet 20 passes in close proximity to indexing coil 19 thereby activating indexing coil 19 sending an electrical signal along electrical wires 21. The signal is processed by monitoring means 22, which in the preferred embodiment is a microprocessor or computer. Microprocessor or computer 22 monitors or controls the rotational speed of the motor 12 and hence the rotational speed of rotor 3. With a known rate of revolution of rotor 3, and through monitoring the activation of indexing coil 19 by rotating indexing magnet 20, the precise position of the indexing magnet 20 can be determined at any point in time. Accordingly, by positioning eddy current probe 10 a known distance from indexing magnet 20 on the inner surface of rotor 3, the precise position or location of eddy current probe 10 can be determined at any particular point in time.

Eddy current probe 10 includes a coil 23 (which may be absolute or differential) connected to a source of electricity (typically alternating current frequency) through electrical wires 24. Since eddy current probe 10 is mounted on housing rotor 3, and as rotor 3 is rotated about housing stator 4 during operation, it is necessary to employ means 25 to electromagnetically bond eddy current probe 10 to housing stator 4. As shown in FIG. 1, means 25 comprises a pair of pot shaped ferromagnetic cores or disks 26 and 27, with the lower core or disk 26 connected to housing rotor 3 and the upper core or disk 27 connected to housing stator 4. Although disks 26 and 27 could function as simple slip rings to electromagnetically bond eddy current probe 10 to housing stator 4, in the preferred embodiment disks 26 and 27 each comprise one half of a rotary transformer 28. That is, lower disk 26 comprises the rotor portion of rotary transformer 28 while upper disk 27 comprises the stator portion of rotary transformer 28. Rotary transformer 28 also includes upper windings 29 on the transformer stator 27 and lower windings 30 on the transformer rotor 26. Preferably disks 26 and 27 of rotary transformer 28 are comprised of a low loss ferromagnetic material.

In the preferred embodiment, electrical wires 24 from eddy current probe 10 are connected to the lower windings 30 on transformer rotor or disk 26. A further set of electrical wires 31 connect the upper windings 29 on transformer stator or disk 27 to the microprocessor or computer 22. In this configuration, impedance changes that may occur in eddy current probe 10 while in use will effect the electromagnetic parameters of rotary transformer 28. Accordingly, through monitoring the electromagnetic parameters of rotary transformer 28 it is possible to detect impedance changes in eddy current probe 10, such as those that are created when the probe passes over a flaw in the material being tested.

Figure 2:
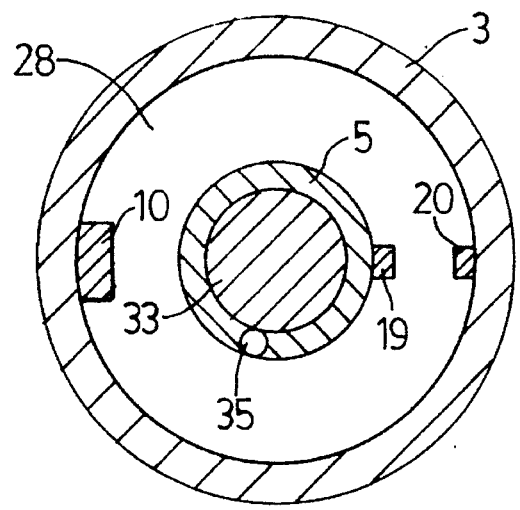
FIG. 2 is a bottom view of the apparatus.

Referring once again to FIG. 1, ultrasonic probe 5 is shown as comprising an ultrasonic transducer 32 having a piezo-crystalline base 33 and an internal dampening material 34. For protection, the base 33 is enclosed in a protective casing 38. A pair of electrical wires 36 connect ultrasonic probe 5 to the microprocessor or computer 22. FIG. 2, shows the lower end of ultrasonic probe 5 to be generally circular in section, however, other configurations could equally be used.

The preferred usage of ultrasonic probe 5 requires a coupling fluid or gel to be applied between ultrasonic probe 5 and the material being tested. Most typically the coupling fluid or gel is water or an aqueous composition that is delivered to the space between the probe and the testing material. To accomplish this, the present invention provides for means 35 to deliver coupling fluid or gel to the lower end of the ultrasonic probe 5. Means 35 comprises an internal tube running through ultrasonic probe 5 and ending at the lower end of the probe, as can also be seen from FIG. 2. During operation of the invention, coupling fluid or gel passes through tube 35 and onto the surface of the testing material. By routing tube 35 through ultrasonic probe 5, the tube is protected from damage and does not interfere with the rotational movement of rotor 3.

Figure 3:
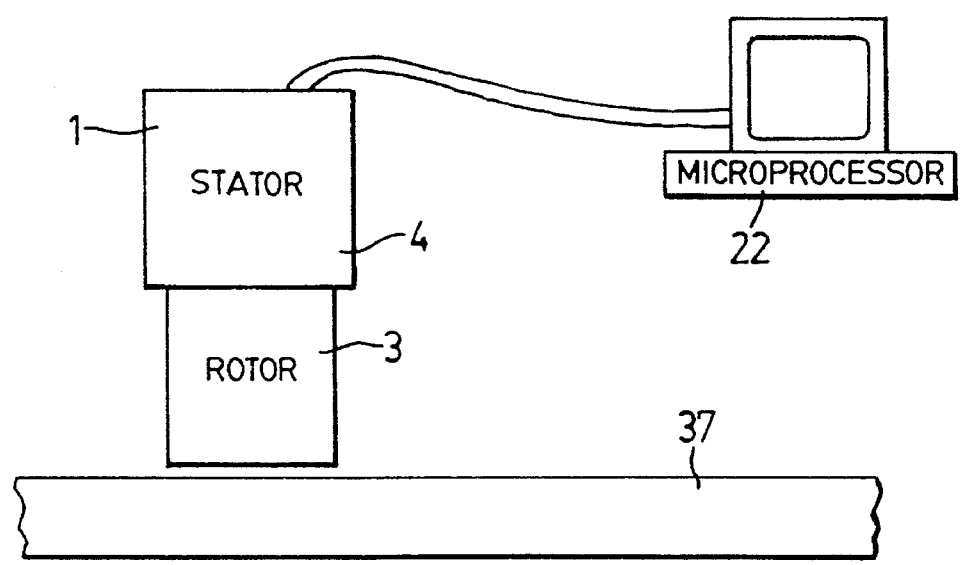
FIG. 3 is a schematic view of the apparatus as it would appear while in use.

Looking now at FIGS. 1 and 3 together, we see the testing device 1 in use on a sheet 37 of material to be tested for flaws. The electrical wires from ultrasonic probe 5, indexing coil 19, and rotary transformer 28 (being 36, 21, and 31 respectively) are shown as connected to microprocessor or computer 22. Microprocessor or computer 22 acts as a means to monitor signals from ultrasonic probe 5 and indexing coil 19, as well as a means to monitor the electromagnetic characteristics of rotary transformer 28, and hence indirectly monitor eddy current probe 10. As discussed previously, coupling fluid or gel passes through tube 35 and onto surface 37 next to ultrasonic probe 5. To operate the device 1, motor 12 (also monitored or controlled by microprocessor or computer 22) is activated causing housing rotor 3 to rotate about housing stator 4. As a result of this rotation, eddy current probe 10 is rotated about ultrasonic probe 5 and rotary transformer 28 is engaged. In the preferred embodiment where indexing magnet 20 is also mounted on rotor 3, indexing coil 19 is activated with each revolution of rotor 3 sending a signal to microprocessor or computer 22. With a known speed of rotation of rotor 3, and with the receipt of signals from indexing coil 19, the precise location of eddy current probe 10 can be determined at any point in time.

As eddy current probe 10 passes over the surface 37 eddy currents are induced in the testing material. These eddy currents in turn produce counter magnetic fields that impede the magnetic field generated by probe 10. Should the probe 10 pass over imperfections or flaws in the testing material, the production of eddy currents in the material is resisted having the effect of altering the normal feed back to probe 10 caused by the eddy currents in the testing material. Therefore, through monitoring the electromagnetic parameters of the rotary transformer 28, the microprocessor or computer 22 is able to determine impedance changes that occur in the eddy current coil 23 and hence determine the existence of flaws in the testing material. Since the position of the eddy current probe is known through the aid of indexing means 18, the precise position of a flaw that is detected in this manner can be determined.

While eddy current probes are generally effective in detecting defects or flaws which are vertically oriented, they are somewhat less effective for detecting horizontal flaws or surface imperfections. For this reason ultrasonic probe 5 operates in conjunction with eddy current probe 10. As eddy current probe 10 induces eddy currents in the testing material, ultrasonic probe 5 subjects the testing material to a beam of ultrasonic energy. Reflected signals received back by probe 5 are then monitored by microprocessor or computer 22.

Eddy current testing can be accomplished at a considerably faster rate than ultrasonic testing and hence the movement of the ultrasonic probe 5 across the surface 37 is much slower than the rotational movement of eddy current probe 10. Since ultrasonic probe 5 is stationary relative to eddy current probe 10, and as ultrasonic probe 5 is moved across the surface 37 relatively slowly, it will be apparent that any defects or flaws that are detected by probe 5 will be located immediately beneath it.

Through moving testing device 1 across surface 37, the material is systematically subjected to both eddy current and ultrasonic analysis. In operation, a grid pattern would typically be used to ensure complete coverage of the entire surface. Use of the invention in this manner results in a thorough analysis for flaws and defects without deleteriously affecting the testing material. The combined use of eddy current and ultrasonic probes provides the operator with the specific advantages associated with each probe. The unique structure, as disclosed and described by this invention, is designed to accommodate and put these probes into operation in a manner that ensures efficient testing, higher coverage, higher local sensitivity and the reliable location of defects.

It is to be understood that what has been described are the preferred embodiments of the invention and that it is possible to make variations to these embodiments while staying within the broad scope of the invention. Some of these variations have been discussed while others will be apparent to those skilled in the art to which this invention relates. For example, while reference has been made to the use of an indexing coil 19 and an indexing magnet 20, indexing means 18 could equally be an encoding device located within rotary transformer 28. Indexing coil 19 could also be mounted on rotor 3 with indexing magnet 20 mounted on ultrasonic probe 5 or stator 4, opposite to that as described above. Furthermore, although the invention has been described as having a single eddy current probe and a single ultrasonic probe, multiple eddy current and ultrasonic probes could equally be employed.

We claim:

1. An apparatus for non-destructively testing for flaws in materials, the apparatus comprising:

(a) a housing assembly for passage over the surface of said material to be tested, said housing assembly including a rotor and a stator;

(b) an ultrasonic probe, fixedly mounted on said stator of said housing assembly, for transmitting ultrasonic energy to said material to be tested and for receiving ultrasonic energy reflected back toward said ultrasonic probe;

(c) an eddy current probe, mounted on said rotor of said housing assembly, for the generation of eddy currents in said material to be tested; and, (d) rotating means for rotationally moving said eddy current probe about said ultrasonic probe.

2. The apparatus as claimed in claim 1 including means to monitor signals from said ultrasonic probe and means to monitor signals from said eddy current probe to detect flaws in said material to be tested.

3. The apparatus as claimed in claim 2 including indexing means to monitor the rotational position of said rotating eddy current probe.

4. The apparatus as claimed in claim 3 having means to electromagnetically bond said eddy current probe on said housing rotor to said housing stator.

5. The apparatus as claimed in claim 4 wherein said means to electromagnetically bond said eddy current probe on said housing rotor to said housing stator comprises a pair of disks, one of said disks being connected to said stator of said housing and the other of said disks being connected to the rotor of said housing.

6. The apparatus as claimed in claim 5 wherein said indexing means comprises an indexing coil attached to said ultrasonic probe and an indexing magnet attached to said housing rotor, such that rotation of said housing rotor about said housing stator causes said indexing magnet to activate said indexing coil once per revolution of said housing rotor about said housing stator.

7. The apparatus as claimed in claim 5 wherein said indexing means comprises an indexing coil attached to one of said housing rotor and said housing stator, and an indexing magnet attached to the other of said housing rotor and said housing stator, such that rotation of said housing rotor about said housing stator causes said indexing magnet to activate said indexing coil once per revolution of said housing rotor about said housing stator.

8. The apparatus as claimed in claim 7 having means to monitor said indexing coil and thereby the rotational position of said housing rotor relative to said housing stator.

9. The apparatus as claimed in claim 8 wherein said means to electromagnetically bond said eddy current probe on said housing rotor to said housing stator comprises a rotatory transformer, and wherein said disks comprise a stator and a rotor of said rotary transformer, said transformer stator being attached to said housing stator and said transformer rotor being attached to said housing rotor.

10. The apparatus as claimed in claim 9 wherein signals from said eddy current probe alter the electromagnetic characteristics of said rotary transformer.

11. The apparatus as claimed in claim 10 including means to monitor the electromagnetic characteristics of said rotary transformer and thereby monitor signals received from said eddy current probe.

12. The apparatus as claimed in claim 11 wherein said means to monitor signals from said ultrasonic probe, said means to monitor signals from said eddy current probe, said means to monitor said indexing coil and said means to monitor the electromagnetic characteristics of said rotary transformer, comprise a computer or microprocessor.

13. The apparatus as claimed in claim 12 wherein said rotating means includes a motor to rotate said housing rotor and thereby rotationally move said eddy current probe about said ultrasonic probe.

14. The apparatus as claimed in claim 13 wherein said ultrasonic probe includes means for the delivery of coupling fluid or gel to the surface of said ultrasonic probe and onto said surface to be tested.

15. The apparatus as claimed in claim 14 wherein said means for delivering said coupling fluid or gel to the surface of said ultrasonic probe comprises an internal tube ending adjacent to the lower surface of said ultrasonic transducer.

16. The apparatus as claimed in claim 15 wherein said ultrasonic probe includes an ultrasonic transducer having a piezo-crystalline base and internal dampening material.

17. The apparatus as claimed in claim 16 wherein said rotary transformer is comprised of a low loss ferromagnetic material and said disks are pot shaped ferromagnetic cores.

18. A method for non-destructively testing for flaws in materials, the method comprising the steps of:

(a) passing a housing assembly containing an ultrasonic probe over the surface of said material to be tested;

(b) simultaneously rotating an eddy current probe, directed to the surface of the material to be tested, about said ultrasonic probe at a fixed and known rate of revolution;

(c) monitoring the position of said rotating eddy current probe relative to said ultrasonic probe through the use of an indexing means operating between said ultrasonic and said eddy current probes; and, (d) monitoring the output signals from said ultrasonic and said eddy current probes.

19. The method as claimed in claim 18 comprising the further step of applying coupling fluid or gel between said ultrasonic probe and the surface to be tested.

20. The method as claimed in claim 19 including the step of electromagnetically connecting said eddy current probe to said housing through the use of a rotary transformer.

21. The method as claimed in claim 20 comprising the further step of monitoring the electromagnetic properties of said rotary transformer as a means of detecting impedance changes in the coil of said eddy current probe to detect flaws in said material being tested.

22. The method as claimed in claim 21 used to detected flaws in metallic materials.

* * * * *